United States Patent [19]

Liu

[11] Patent Number: 4,950,231
[45] Date of Patent: Aug. 21, 1990

[54] VAGINA CLEANSING DEVICE

[76] Inventor: Su-Haw Liu, No. 41-2, Lane 24, Shin Kang Rd., Lin-Ya District, Taiwan

[21] Appl. No.: 503,117

[22] Filed: Mar. 30, 1990

Related U.S. Application Data

[63] Continuation of Ser. No. 245,804, Sep. 19, 1988, abandoned.

[51] Int. Cl.$^5$ .............................................. A61M 3/02
[52] U.S. Cl. .................................... 604/39; 604/257; 604/279
[58] Field of Search ....................... 600/29; 604/39-42, 604/82-85, 113, 114, 187, 271, 275, 279, 280, 283, 288, 257

[56] References Cited

U.S. PATENT DOCUMENTS

| | | | |
|---|---|---|---|
| 540,213 | 5/1895 | Morrison | 604/41 |
| 2,043,882 | 6/1936 | Cheek | 604/42 |
| 3,044,465 | 7/1962 | Anderson et al. | 604/83 |
| 3,533,409 | 10/1970 | Greer | 604/83 |
| 4,178,931 | 12/1979 | Lind et al. | 604/151 |
| 4,682,979 | 7/1987 | Girouard | 604/151 |

Primary Examiner—C. Fred Rosenbaum
Assistant Examiner—William W. Lewis
Attorney, Agent, or Firm—Larson and Taylor

[57] ABSTRACT

A vagina cleansing device has a cleansing bar, a connecting tube and a control case. The cleansing bar can be inserted in the vagina properly, through the connecting tube, the controlling case having a water tank storing water or sterilizing solution, in order to supply water or the water mixed with sterilizing solution in washing or sterilizing the vagina.

3 Claims, 2 Drawing Sheets

VAGINA CLEANSING DEVICE

This application is a continuation, of application Ser. No. 07/245,804 filed 9/19/88, now abandoned.

BACKGROUND OF THE INVENTION

This invention concerns a cleansing device for women to use in washing or sterilizing their vaginas. As the vagina may give out an odor because of normal secretion of abnormal secretion caused by bacteria, it is quite a necessity of women to wash it daily with clean water or some kind of sterilizing solution or sometimes to prevent pregnancy.

SUMMARY OF THE INVENTION

But so far such a cleansing device is hardly seen in the market. The object of this invention is to provide a vagina cleansing device. It comprises a cleansing bar, a trumpet-shaped cap, a connecting tube and a control case as its main parts.

The cleansing bar is made of a long small-diameter bar provided with an inner longitudinal passage for water to pass from the rear end to the front section bored with a plurality of small spewing holes for water to spew out inside the vagina.

The trumpet-shaped cap is shaped like a trumpet from the front extending wider and wider to the rear and is provided with an inner opening at the front end to couple around and move along the outer face of the rear of the cleansing bar and to be fixed firmly thereon adjustable in its location by means for positioning pegs screwing in screw holes in the cap and sticking against straight grooves in the face of the bar. Therefore, the bar can be inserted in the vagina as properly as the user needs.

The connecting tube made of a soft material has a female-threaded ring at one of its ends for connecting with the male-threaded end of the cleansing bar and a nut at the other end for connecting with a faucet of water supply or a water outlet in the control case to get water or the water mixed with sterilizing solution for cleansing or sterilization.

The control case is provided with a water tank, a sucking pump, a heater, an inlet and outlets to supply water or the water mixed with a medical solution to the cleansing bar through the connecting tube. Besides, the water stored in the water tank can be heated to a warmer temperature in case this device should be used in a cold weather.

BRIEF DESCRIPTION OF THE DRAWINGS

This invention will now be described in detail with reference to accompanying drawings wherein.

DETAILED DESCRIPTION OF THE INVENTION

Figure 1:
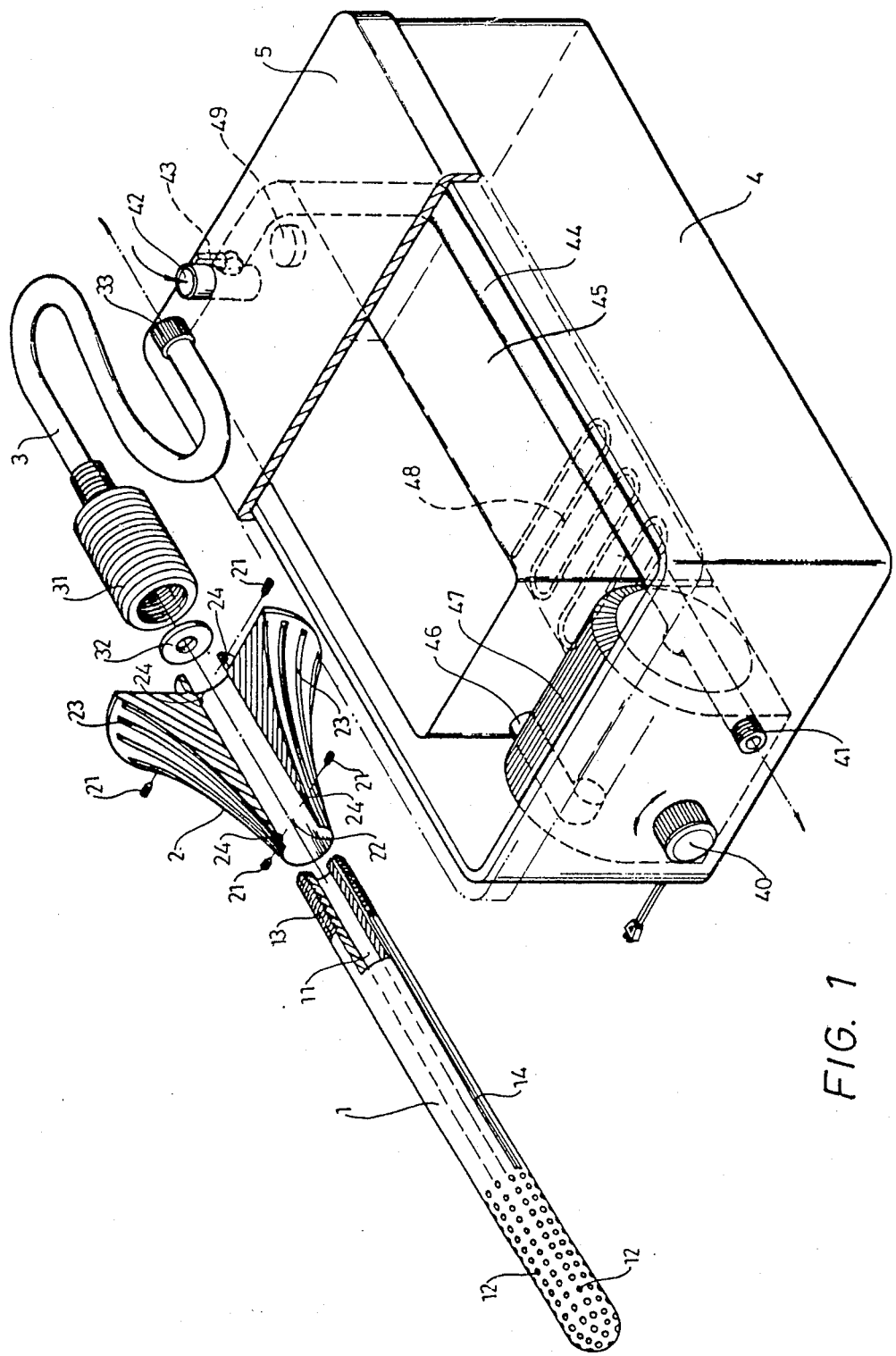
FIG. 1 is an exploded perspective view of the vagina cleansing device in accordance with the present invention.
Figure 2:
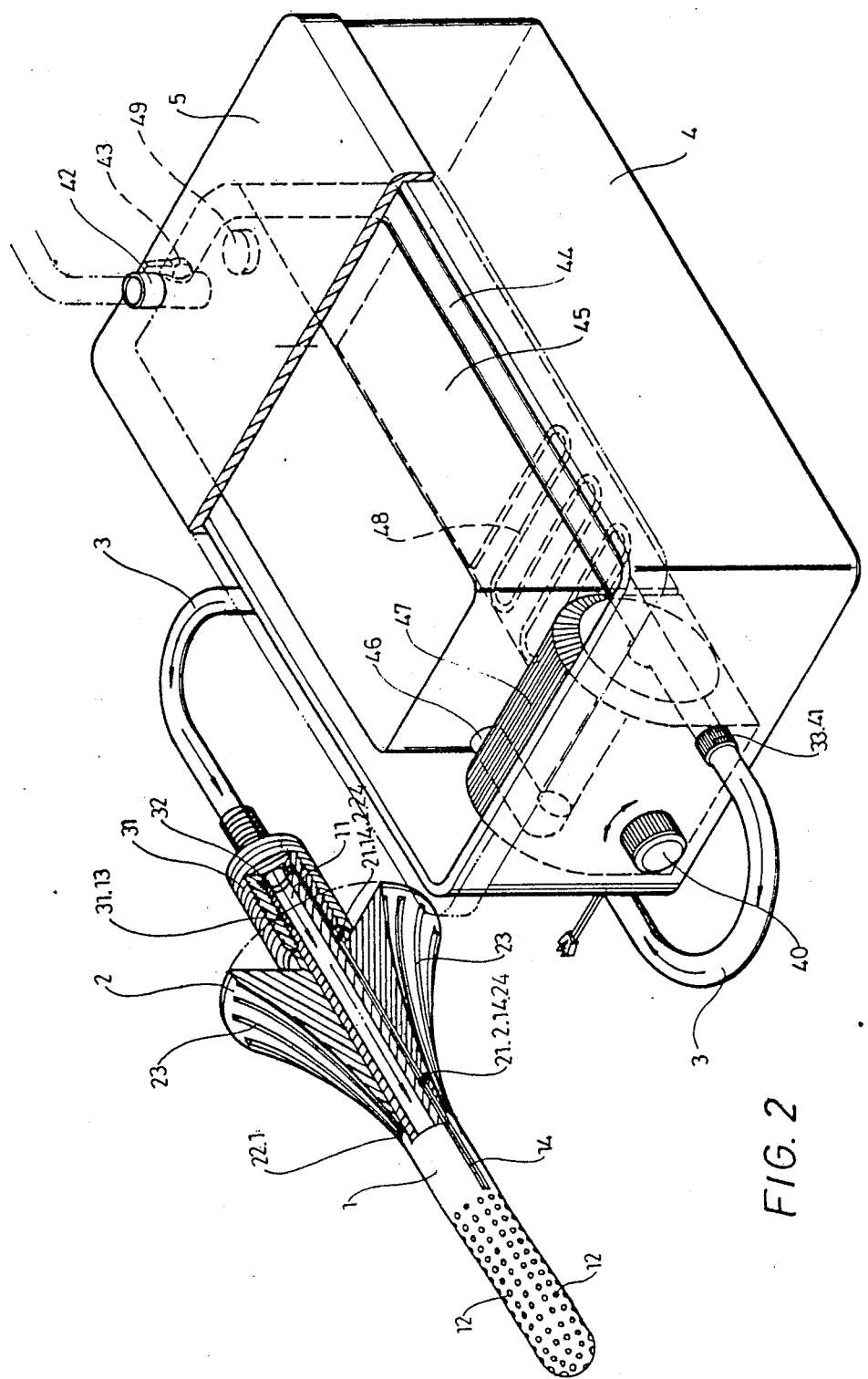
FIG. 2 is a perspective view of the vagina cleansing device assembled together for practical use in accordance with the present invention.

This vagina cleansing device, as shown in FIG. 1, comprises a cleansing bar 1, a trumpet-shaped cap 2, a connecting tube 3 and a control case 4 as its main parts.

The cleansing bar 1 is a round bar of a comparatively small diameter, and provided with a longitudinal inner water passage 11, a plurality of small spewing holes 12 in the front section, male-threads 13 on the rear end and straight grooves 14 on the middle and the rear sections separately at both sides. The water passage 11 is for water to pass through from the rear end to the front section, the spewing holes 12 are for the water passing through the water passage 11 to be spewed into the vagina, the male-threads 13 for screwing with the female-threaded ring 31 of the connecting tube 3, and the grooves 14 are for positioning pegs 21 to insert through for positioning the trumpet-shaped cap 2 around the cleansing bar 1.

The trumpet-shaped cap 2 is shaped as a trumpet from the front extending gradually wider to the rear and provided with an inner opening 22 at the front end and two peg holes 24 separately in the front and the rear sections and a plurality of longitudinal grooves 23 on the face. The inner opening 22 is to be coupled around the rear section of the cleansing bar 1 so that the trumpet-shaped cap 2 can slide along the bar 1 for adjusting its position in relation to the bar 1 and the peg holes 24 can be screwed through by the positioning pegs 21 which also can stick against the grooves 14 of the bar 1. Besides, the pegs 21 should have flat heads to hide inside the body of the trumpet-shaped cap 2 lest they should hurt the user's body. The longitudinal grooves 23 are for the water spewed out in the vagina to flow out.

The connecting tube 3 is a common soft one and provided with a female-threaded ring 31 and a packing 32 at one end and a nut 33 at the other end. The female-threaded ring 31 screws with the male threads of the cleansing bar 1 and provided with the packing 32 to prevent water leakage, and the nut 33 can be connected with either a faucet of water supply or a water outlet 41 of the control case 4 for being supplied with water or the water mixed with sterilizing solution.

The control case 4 is provided with a water outlet 41, a water inlet 42 and a switch 43. The water inlet 42 can receive water which may pass through a water tube 44 and out of the water outlet 41 or may flow into a water tank 45 by handling the switch 43. The water stored in the tank 45 can be drawn out through a water outlet 46 by a sucking pump 47 and flow into the water tube 44. An electric heater 48 is provided under the bottom of the tank 45 to heat the water therein, if necessary. A cap 49 on an aperture in the top face of the tank 45 is provided for pouring sterilizing solution in to be mixed with the water.

The sucking pump 47 is controlled by a button 40 for changing its speed and whereby the quantity of the water flowing out of the water outlet 41 can be adjusted as properly as needed.

In using this device, the trumpet-shaped cap 2 can be adjusted in its location on the cleansing bar 1 and anchored by positioning pegs 21 firmly around the bar 1 so that the length of the bar 1 to be inserted in the vagina may be properly adjusted according to the user's need. Then the water can be made to flow through the connecting tube 3, the passage 11 and then to spew out of the spewing holes 12 of the cleansing bar 1, and if necessary, the water mixed with sterilizing solution can be used drawn from the control case 4 for sterilization of the interior of the vagina. Besides, in a cold weather, the heater 48 in the control case 4 can be used to warm up the water in the tank 45 to a proper temperature for comfortable cleansing.

If this device is wanted to be put away after use, the cleansing bar 1, the trumpet-shaped cap 2 and the connecting tube 3 can be disconnected and put in the control case 4 beside the tank 4 after the lid 5 is taken off.

What is claimed is:

1. A vagina cleaning device comprising: an enlongated cleansing bar having a long small diameter and having an inner longitudinal water passage and a plurality of outlet openings at an outer end thereof; a connecting tube being connected to a rear end of the cleansing bar and connected at its other end to a source of cleansing water; a trumpet shaped cap increasing in (a) diameter from its front end to its rear end, (b) having a plurality of longitudinal grooves on its outer face from the front end to the rear end to facilitate the flow of water which has passed out through the outlet openings of the cleansing bar, (c) having a round opening at its front end to fit snugly and adjustably around the outer surface of the cleansing bar and (d) being adjustably connected thereto such that the length of the bar to be inserted into the vagina is adjustable according to the needs of a user; and a control case having a water tank for storing water to be fed to the connecting tube and a pump for drawing water in the tank through a control case outlet to the connecting tube, said control case having an inlet, and means for directing water received at said control case inlet either to the tank or bypassing the tank, directly to the control case outlet, and said control case having room therein beside the tank for storing the cleansing bar, cap and connecting tube.

2. A vagina cleaning device according to claim 1, said tank further including a heating means for heating the water in the tank before said water is delivered to the connecting tube.

3. A vagina cleansing device according to claim 1, wherein said cleansing bar includes at least one longitudinal groove along an outer surface adjacent an inner end of said cleansing bar; and further including positioning pegs which are threadably received in said cap and which engage said groove of said cleansing bar for adjustably connecting the cap to the cleansing bar.

* * * * *